United States Patent
Morrison et al.

Patent Number: 5,364,374
Date of Patent: Nov. 15, 1994

[54] MICRONEEDLE FOR INJECTION OF OCULAR BLOOD VESSELS

[75] Inventors: John C. Morrison; Chester G. Moore, both of Portland, Oreg.

[73] Assignee: State of Oregon, Portland, Oreg.

[21] Appl. No.: 126,683

[22] Filed: Sep. 24, 1993

Related U.S. Application Data

[63] Continuation of Ser. No. 866,561, Apr. 10, 1992, abandoned.

[51] Int. Cl.⁵ ............................................. A61M 5/32
[52] U.S. Cl. ..................................... 604/272; 604/52; 604/239; 604/264; 604/294
[58] Field of Search .............. 604/51, 52, 187, 239, 604/240, 243, 264, 294, 53, 164, 257, 272, 280, 177

[56] References Cited

U.S. PATENT DOCUMENTS

| | | |
|---|---|---|
| 2,531,667 | 11/1950 | Brent ........................ 604/53 |
| 3,986,834 | 10/1976 | Steinbrink et al. . |
| 4,050,316 | 9/1977 | Rapoza . |
| 4,078,892 | 3/1978 | Steinbrink et al. . |
| 4,191,176 | 3/1980 | Spina et al. ............... 604/51 |
| 4,349,022 | 9/1982 | Ishikawa ................... 604/177 |
| 4,885,945 | 12/1989 | Chiodo ...................... 65/54 |
| 5,000,732 | 3/1991 | Banks et al. ............... 604/280 |

FOREIGN PATENT DOCUMENTS 2030865  9/1978  United Kingdom ................ 604/280

OTHER PUBLICATIONS

Toth et al., "Ultramicrosurgical Removal of Subretinal Hemorrhage in Cats," 13 Nov., 1991, pp. 175-182 (Published in American Journal of Ophthalmology 113:175-182, Feb. 1992.).
Hori et al., 1983, Gann 74 122-127.

Primary Examiner—C. Fred Rosenbaum
Assistant Examiner—N. Kent Gring
Attorney, Agent, or Firm—Allegretti & Witcoff, Ltd.

[57] ABSTRACT

This invention is a device for microvascular injection and a method for treating glaucoma using the device. The device comprises a reservoir attached to a blunted needle connected to a flexible tapered tubing, at the end of which is positioned a microneedle or micropipette for inserting into small blood vessels. The invention also provides a method for treating glaucoma and other diseases wherein microinjection of disease-ameliorating drugs into small blood vessels and their capillary beds would be therapeutically effective.

11 Claims, 5 Drawing Sheets

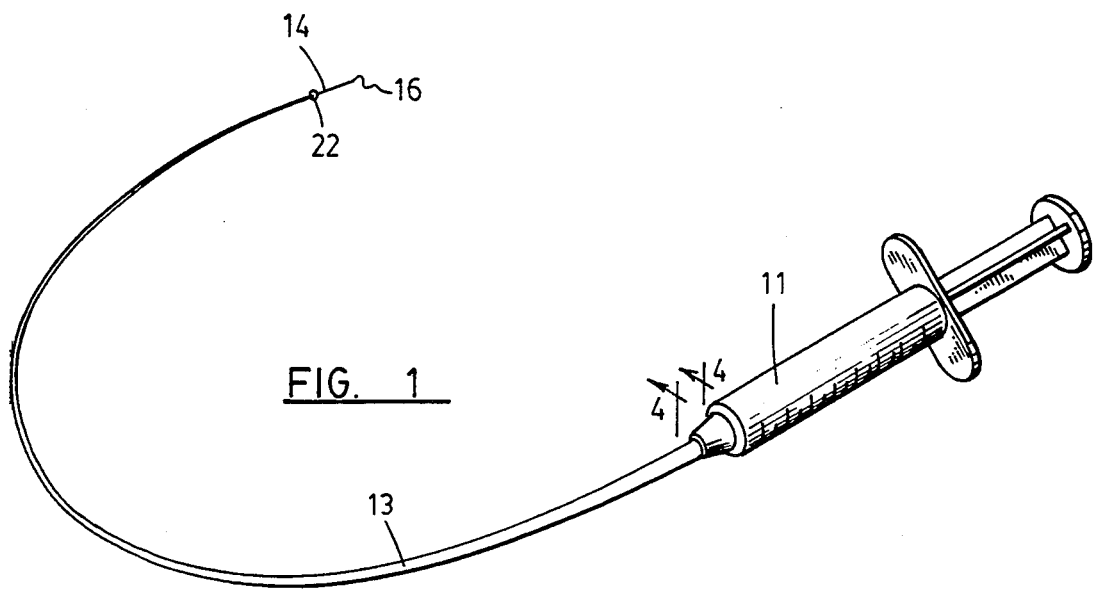
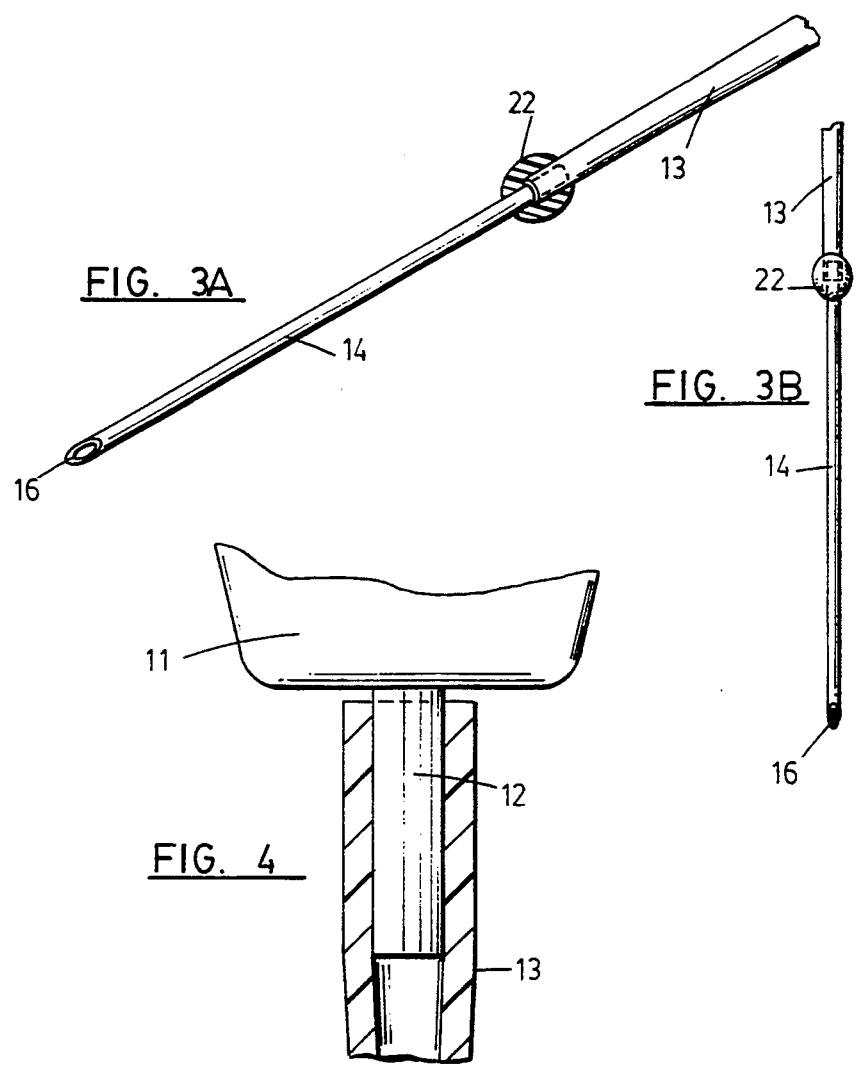

MICRONEEDLE FOR INJECTION OF OCULAR BLOOD VESSELS

This invention was made with government support under Grant #1-2-409-540 by the Veterans' Administration. The government has certain rights in the invention.

This application is a continuation of application Ser. No. 07/866,561, filed Apr. 10, 1992 now abandoned.

BACKGROUND OF THE INVENTION

1. Field of The Invention

The present invention relates to a device which enables microvascular injections and manipulations directly into delicate and otherwise inaccessible blood vessels such as the capillary beds of the eye, thus providing means for more effectively treating diseases of the eye such as glaucoma.

2. Background of the Invention

Glaucoma is an ophthalmic disease which is manifested in most patients by an increase in intraocular pressure (normally equal to 5-25 mm of Hg) sufficient to cause degeneration of the optic nerve and defects in the visual field. It is a major cause of preventable blindness, affecting 2% of the adult population. Clinically, it is characterized by a specific type of optic nerve damage which accompanies the pathological increase in intraocular pressure. Most instances of elevated intraocular pressure are due to increased resistance to aqueous humor outflow from the trabecular meshwork, a sieve-like ringed structure located at the juncture of the iris and cornea.

Conventional glaucoma therapy concentrates on lowering intraocular pressure, either through eye drops, laser treatments, or surgery, all of which have significant drawbacks. Eye drops have been prescribed (either alone or usually in combination) either to inhibit the secretion of aqueous humor by the ciliary processes ("beta-blockers") or to improve escape of aqueous humor from the eye (such as pilocarpine, the miotic). To be effective, however, these drugs need to be administered in highly concentrated dosages because of poor penetration of the drugs into the eye. The administration of these drugs in such highly concentrated dosages creates a strong potential for ocular and systemic side effects, since much of these drugs drain into the nose and are absorbed into the bloodstream through the nasal lining. This is particularly a problem when the drugs must be administered on a continuous basis over a patient's lifetime.

Laser treatment is often used as an alternative or in addition to drug treatment, but the results are variable and often transient. The best current surgical treatment involves creating a channel for the fluid to escape out of the eye, thereby lowering the intraocular pressure. Although effective in controlling the eye pressure, this surgery has significant potential for producing sight-threatening complications including infection and bleeding, especially immediately after surgery (when eye pressure suddenly and dramatically decreases).

Accordingly, there is a need for new therapeutic approaches to lower intraocular pressure, using agents to alter the function of the trabecular meshwork permanently or at least on a prolonged basis. An important step towards such a therapy would be direct delivery of the agent into the trabecular meshwork. This approach would eliminate the problems of ocular or systemic side effects which have been encountered heretofore with the chronic therapeutic use of eye drops given in highly concentrated dosages. In addition, the margin of safety of such a therapy would be greatly improved over surgery if the administered drug acted gradually to lower intraocular pressure.

Micropipettes have been used in diagnostic procedures.

U.S. Pat. No. 3,986,834 discloses a kit in which a micropipette may be included for transferring reagents undergoing analysis of blood urea.

U.S. Pat. No. 4,050,316 discloses the use of an aspirator with a micropipette.

U.S. Pat. No. 4,078,892 discloses the use of a micropipette in transforming plasma into a diazo reagent for the determination of bilirubin.

Frenkel et al., 1989, Vestn. Ofthalmol. 105: 27-29 disclose the optimal shape of microneedles for suturing solid biological tissues, and the use of such needles for ophthalmological surgery.

Hori et al., 1983, Gann 74: 122-127 disclose the use of micropipetted to partially occlude microvessels without disturbing microcirculation.

SUMMARY OF THE INVENTION

The present invention relates to a device comprising in combination a reservoir, preferably a syringe, most preferably a syringe having a volume of 1-2 cubic centimeters, the syringe having attached thereto a blunt needle, preferably a blunted hypodermic needle. Attached to the needle is a piece of flexible tapered tubing suitable for dispensing ophthalmic solutions; suitable tubing is preferably polyethylene tubing, most preferably PE-50 tubing, tapered to a degree that the wider end of the tubing fits over the blunt needle and the narrower end fits over a microneedle. The microneedle comprises a glass micropipette or a metallic microneedle wherein one end of the microneedle is attached to the narrower end of the tubing. The other end of the microneedle is preferably beveled. The device of the invention is useful for insertion into small blood vessels in vivo, in particular the aqueous vessels leading from the trabecular meshwork of the eye.

The present invention also includes within its scope a method for the treatment of glaucoma using the device provided by the invention.

BRIEF DESCRIPTION OF THE DRAWINGS

FIGS. 1 through 4 are schematics of the device of the present invention.

DETAILED DESCRIPTION OF THE PREFERRED EMBODIMENTS

Figure 2:
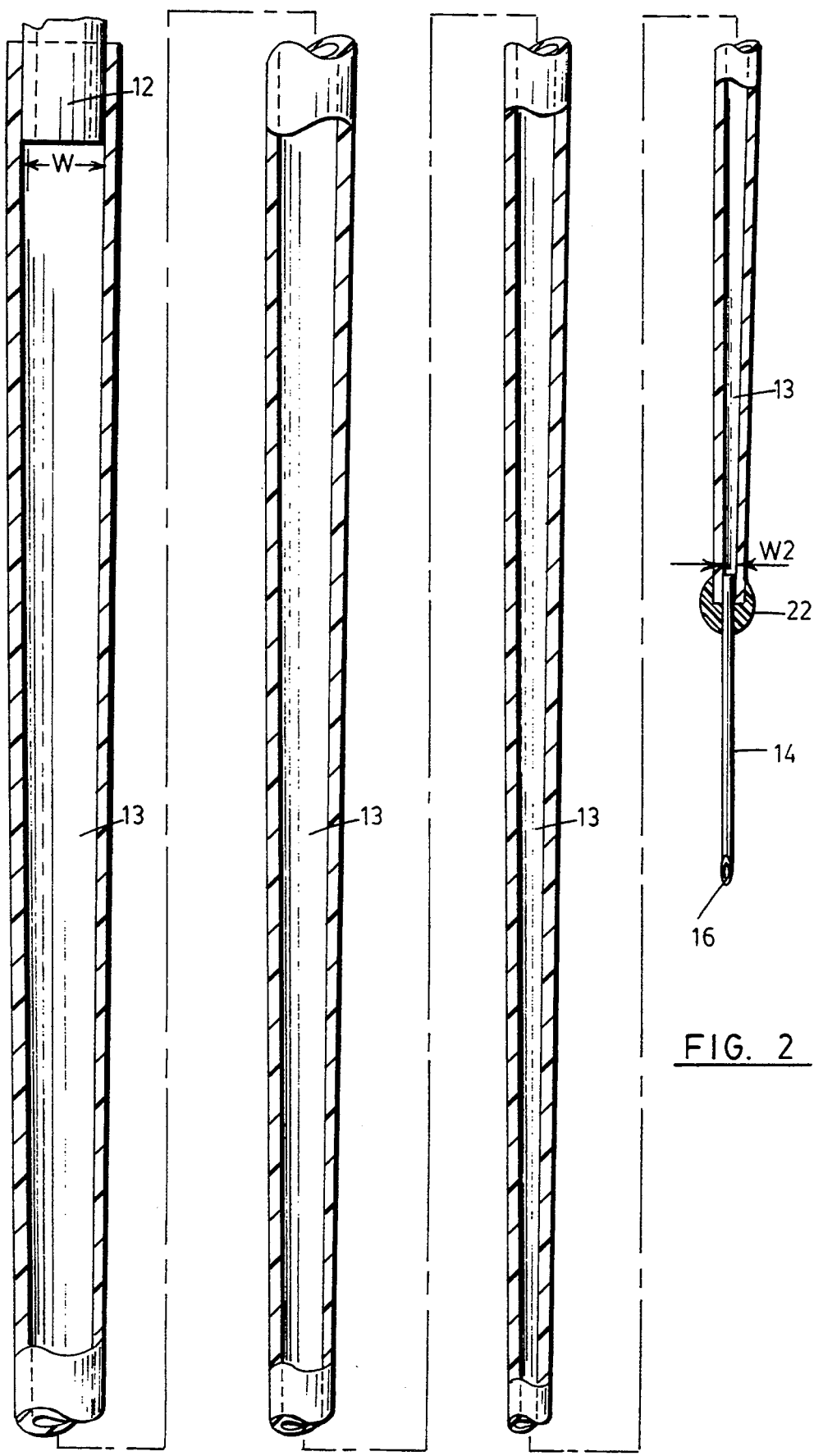
Figures 5A, 5B:
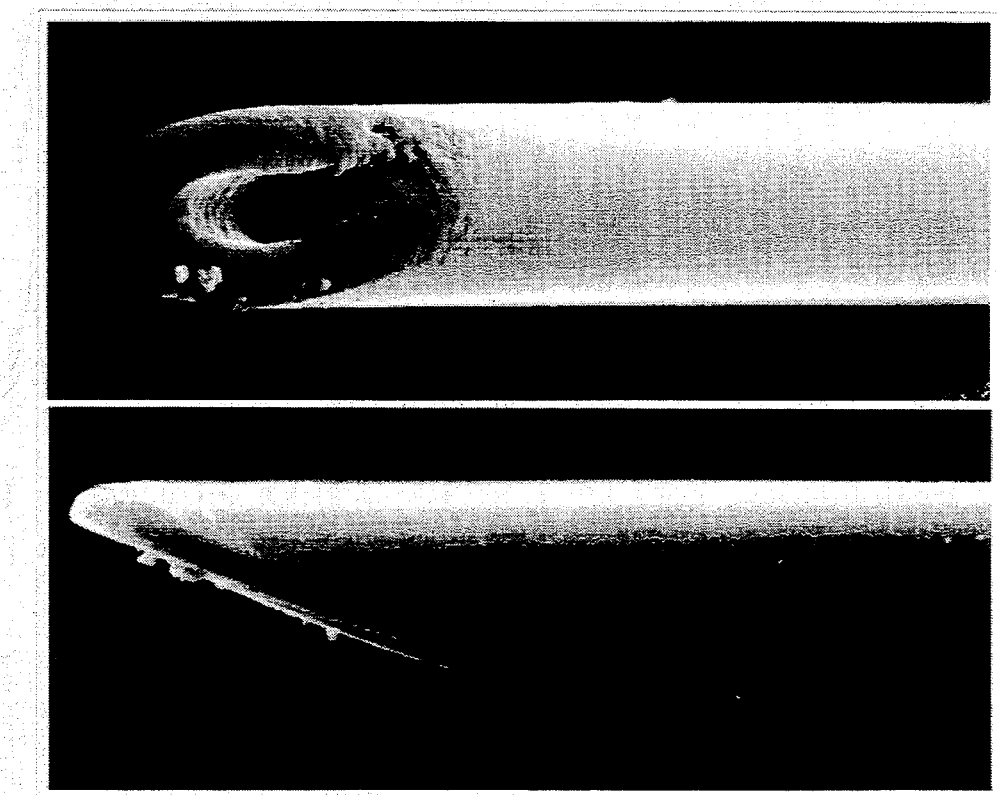
FIGS. 5A and 5B are scanning electron micrographs of a glass microneedle tip which has been beveled and magnified 1000 times.

A complete understanding of the invention may be better obtained by referring to the accompanying drawings, FIGS. 1 to 4 inclusive. In FIG. 1, there is seen a reservoir, preferably having a small-volume plunger-type syringe 11 (most preferably having a volume of 1 to 2 cubic centimeters), having attached at the discharge end a needle 12, preferably a blunted hypodermic needle (FIG. 4). The needle may be made of stainless steel, hyperchrome steel, carbon steel, chromium, nickeloid, platinum, platinumuridium, silver or gold. Attached to the blunted end of the needle is a piece of ophthalmologically acceptable tapered tubing 13 about 6–12 inches in length and constructed of any flexible polymeric materials, including but not limited to polyethylene, polypropylene, and like polymeric materials which are inert chemically. The tubing is tapered to a degree that the wider end of the tubing fits over the blunted hypodermic needle and the narrower end fits over a microneedle (FIG. 2). At the narrower end of the tubing 13, there is positioned a microneedle 14. This aspect of the invention may be seen more clearly in FIG. 3A and 3B. In one embodiment of the invention, the microneedle comprises a drawn or pulled out glass micropipette. In other embodiments, the microneedle is made of any fine material, including but not limited to stainless steel, hyperchrome steel, carbon steel, chromium, nickeloid, platinum, platinumuridium, silver or gold. Suitable needles may be about 20 to 100 microns wide and 1–5 mm long. In a preferred embodiment, the tip of the microneedle is beveled, as shown in FIGS. 5A and 5B. The flexible tubing is operatively linked at one end to the hypodermic needle and at the other end to the microneedle (FIG. 2). For the purposes of this invention, the term "operatively linked" means physically joined so as to permit fluid flow without leaking. The joints between the needle 12 and the tubing 13 and between the tubing and the micropipette or microneedle 14 are secured to prevent leakage, preferably by glue or other suitable material. At the junction of the needle and the tubing, a small amount of glue or other rigid material forms a rigid spherical gripping means 22 that surrounds the tapered tubing at the junction of the tubing with the microneedle (FIGS. 2 and 3). The gripping means 22 provides a contact point for holding the microneedle with forceps or other suitable instruments. This feature of the invention allows virtually any orientation to be achieved and maintained by the operator during microvascular injection using the device. In a preferred embodiment, the gripping means comprises a ball of glue.

Figure 6:
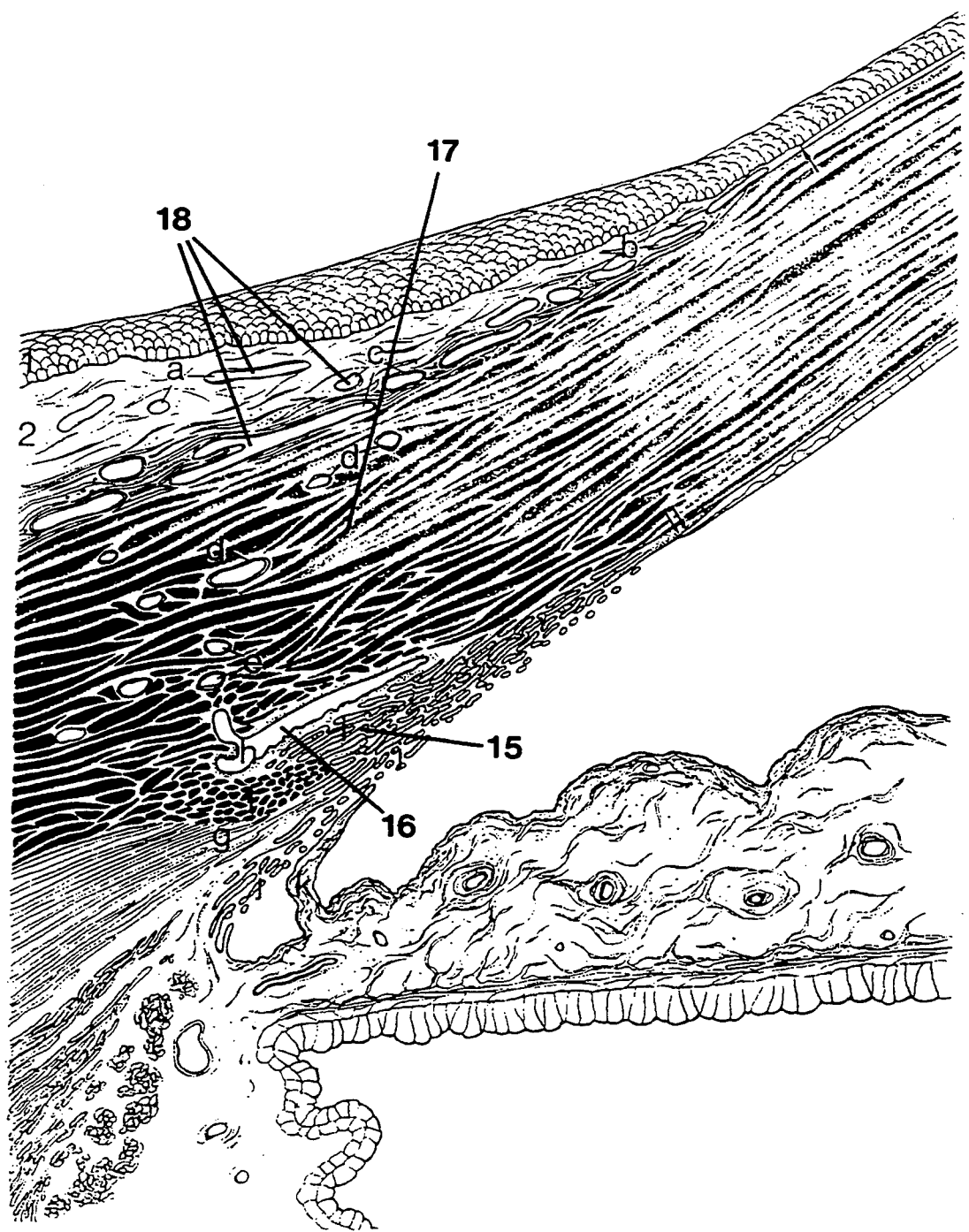
FIG. 6 is an illustration of the relationship of the trabecular meshwork 15 to Schlemm's canal 16 in the normal human eye.
Figure 7:
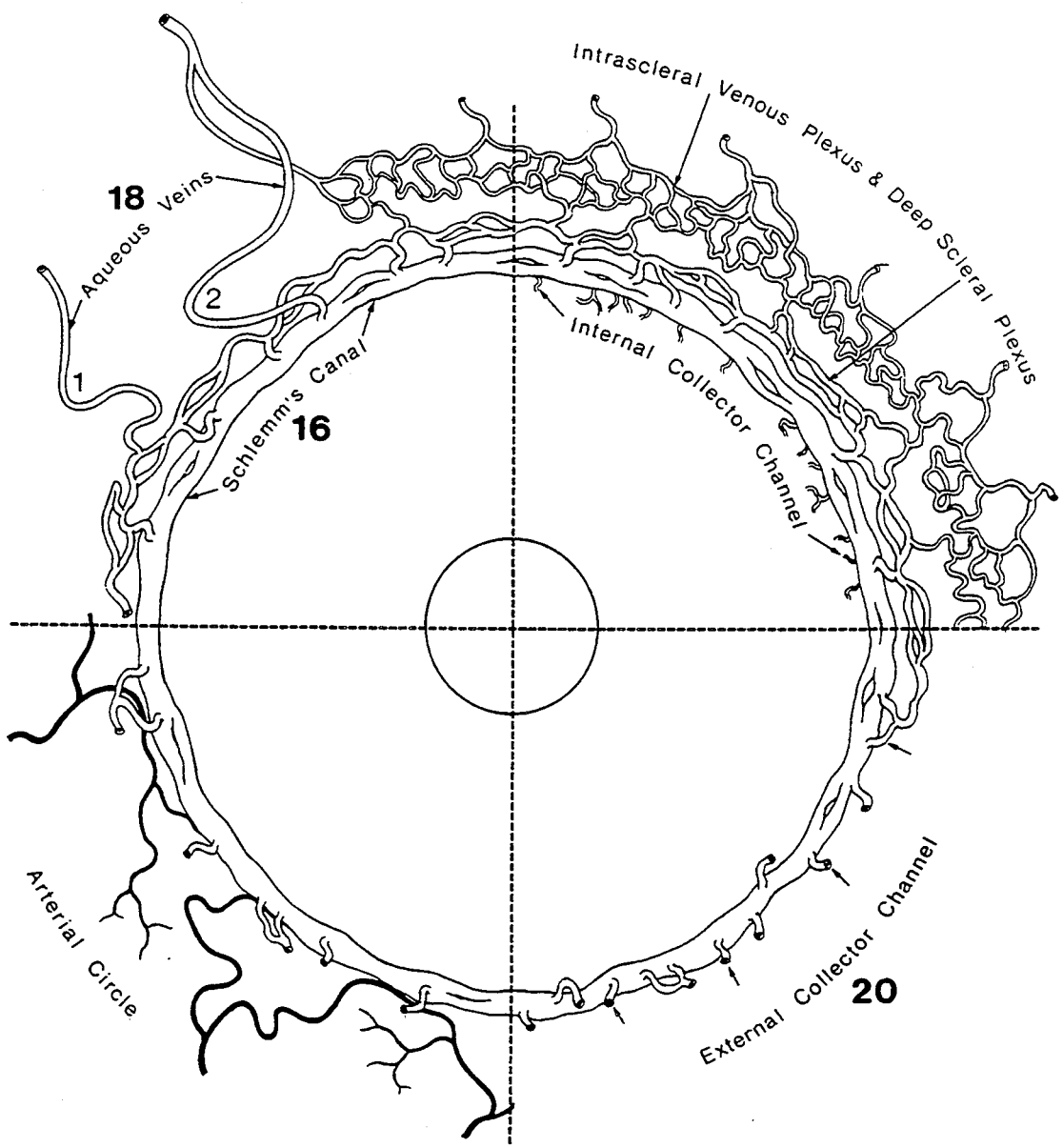
FIG. 7 is a schematic of a diagram of Schlemm's canal and its associated collector channels and their relationship to sclera 17 and aqueous veins 18 located on the surface of the eye.

FIG. 6 illustrates the trabecular meshwork 15 to Schlemm's canal 16 in a normal human eye. Normally, aqueous humor flows through the trabecular meshwork 15 and into Schlemm's canal 16. Schlemm's canal 16 is drained through the sclera 17 into episcleral aqueous veins 18. FIG. 7 illustrates Schlemm's canal 16 and its associated collector channel 20 and their relationship to the aqueous veins 18. Clinically, most of these veins 18 are filled with blood but many are clearly identifiable by a clear column of aqueous humor running beside the red blood cells.

In the practice of the present invention in treating glaucoma, the syringe is filled with an ophthalmic solution containing a therapeutic agent, preferably one which lowers intraocular pressure by reducing resistance to outflow through the trabecular network. The microneedle 14 is inserted into one of the aqueous veins 18, and the plunger of the syringe 11 is depressed allowing the solution to be delivered directly to the trabecular meshwork 15. Using the microneedle 14 according to the present invention allows the direct entry of therapeutic agents into the delicate and otherwise inaccessible trabecular meshwork of the eye. Although the inner diameter of the needle 14 is small, it is sufficiently large to permit the injection of significant amounts of ophthalmic solutions at effective rates (at least 0.1 cc per 15–60 seconds). This is a significant development as the entire volume of the front chamber of the eye is about 0.25 cc.

Depending on the clinical condition of the patient, the microneedle 14 could be inserted with local or in some cases even topical anesthetics, including but not limited to xylocaine and proparacaine-HCl.

In addition to agents designed to reduce trabecular meshwork resistance, other therapeutic agents, [such as antibiotics or antibacterials (such as tetracyclines), steroids (such as hydrocortisone), and the like] may also be delivered to the eye with this device to treat pathological conditions other than glaucoma, such as intraocular infection or inflammation.

While the device of the present invention has been described with particular reference to the eye, it will be obvious to those skilled in the art that this invention has applications in other medical fields whenever direct microsurgical injection is indicated to deliver therapeutic agents to discrete microvascular beds. An example would be neurosurgical oncology when direct injection of potent anticancer agents could be performed to treat otherwise inaccessible tumors. By allowing access to very small blood vessels with their small perfusion beds, the device according to the present invention would allow discrete injection of highly potent therapeutic agents with minimal side effects or damage to normal tissues.

In a commercial embodiment of the present invention, the device is sterilized, preferably by gas sterilization such as by exposure to ethylene oxide gas. The syringe is then filled with a sterile ophthalmic solution using aseptic procedures. The device is then packaged with plastic, such as a low density polyethylene, and sterilized again, preferably with ethylene oxide. Alternatively, the device can be packaged and sterilized prior to filling and the syringe filled with sterile therapeutic agent immediately prior to use.

It should be understood that the foregoing disclosure emphasizes certain specific embodiments of the invention and that all modifications or alternatives equivalent thereto are within the spirit and scope of the invention as set forth in the appended claims.

What we claim is:

1. A device for microvascular injection of a solution into a small blood vessel in vivo, comprising in combination:
   a) a reservoir comprising a syringe and a hypodermic needle;
   b) a flexible tubing having a continuously tapered bore and a first end and a second end, the first end of the flexible tubing being operatively linked to the hypodermic needle, wherein the bore of the flexible tubing is at least about 300 microns in inner diameter at the first end and is sufficient to fit over the hypodermic needle; and
   c) a microneedle having a length of about 1 to about 5 millimeters and an outer diameter of about 20 microns to about 100 microns, and a first end and a second end, the first end of the microneedle being operatively linked to the second end of the flexible tubing, wherein the bore of the flexible tubing is from about 20 microns to about 100 microns in width at said second end and is sufficient to fit over the first end of the microneedle, wherein the microneedle is further characterized by having sides that are not tapered.

2. A device according to claim 1 wherein the second end of the microneedle is beveled.

3. A device according to claim 1 wherein the hypodermic needle is blunted.

4. A device according to claim 1 having rigid spherical gripping means surrounding the tapered bore of the second end of the flexible tubing.

5. A device according to claim 4 wherein the rigid spherical gripping means comprises a bead of glue.

6. A device according to claim 1 wherein the syringe has a volume of 1 to 2 cubic centimeters.

7. A device according to claim 1 wherein the flexible tubing is constructed of polyethylene plastic.

8. A device according to claim 1 in which the syringe contains an intraocular pressure lowering agent.

9. A device according to claim 1 in which the syringe contains an antibacterial agent.

10. A device according to claim 1 in which the syringe contains an anti-inflammatory agent.

11. A device according to claim 1 in which the syringe contains an anti-cancer agent.

* * * * *